United States Patent [19]

Merten et al.

[11] 4,384,142
[45] May 17, 1983

[54] PRODUCTION OF CYCLOHEXYLAMINE

[75] Inventors: Helmut L. Merten, Hudson; Gene R. Wilder, Medina, both of Ohio

[73] Assignee: Monsanto Company, St. Louis, Mo.

[21] Appl. No.: 271,869

[22] Filed: Jun. 9, 1981

[51] Int. Cl.³ .............................................. C07C 85/24
[52] U.S. Cl. .................................... 564/450; 564/451
[58] Field of Search ........................................ 564/450

[56] References Cited

U.S. PATENT DOCUMENTS

| | | | |
|---|---|---|---|
| 2,511,028 | 6/1950 | Whitman | 260/563 |
| 2,606,924 | 8/1952 | Whitman | 260/563 |
| 2,606,925 | 8/1952 | Whitman | 260/563 |
| 2,822,392 | 2/1958 | Illich, Jr. et al. | 260/563 |
| 2,955,926 | 10/1960 | Illich, Jr. et al. | 23/289 |
| 3,347,917 | 10/1967 | Arthur | 260/563 |
| 3,636,108 | 1/1972 | Brake | 260/563 |
| 3,644,522 | 2/1972 | Brake et al. | 260/563 |
| 3,914,307 | 10/1975 | Massie | 260/563 |
| 4,161,492 | 7/1979 | Weissel | 260/563 |

OTHER PUBLICATIONS

Hydrogenation of Aniline to Cyclohexylamine with Platinum Metal Catalysts, Harold Greenfield, Naugatuck Chemical Division of U.S. Rubber Company, J. Org. Chem., vol. 29, pp. 3082-3084.

*Primary Examiner*—Paul F. Shaver
*Attorney, Agent, or Firm*—Gordon B. Seward

[57] ABSTRACT

Cyclohexylamine is produced by the catalytic hydrogenation of aniline. In contact with a ruthenium catalyst and in the presence of from about one to about 8 parts by weight of ammonia, aniline is hydrogenated under an absolute pressure of from about 2 to about 5 MPa at a temperature of from about 160° to about 180° C. High yields and a minimum of byproducts result. The catalyst can be recycled.

8 Claims, No Drawings

PRODUCTION OF CYCLOHEXYLAMINE

BACKGROUND OF THE INVENTION

This invention relates to a process for production of a cyclohexylamine by the catalytic hydrogenation of the corresponding aromatic amine.

The use of ruthenium catalysts in hydrogenating aromatic compounds to produce cyclohexylamines is disclosed in U.S. Pat. No. 2,606,925, in the name of Gerald M. Whitman. This patent shows the reaction of an aromatic compound containing a nitrogen atom attached to the aromatic ring with hydrogen under pressure over a variety of ruthenium catalysts. Pressures of from 1,000 to 10,000 pounds per square inch (6.9 to 69 MPa) are generally used, with temperatures from 20° to 150° C. Typical reactions produced 75% of theoretical yield of the desired cyclohexylamine.

Continuous hydrogenation of aniline to produce cyclohexylamine using a ruthenium catalyst is taught in U.S. Pat. No. 2,822,392, to G. M. Illich et al. Patentees use a temperature of from 200° to 250° C. and hydrogen pressures of from 250 to 10,000 psi (1.7 to 69 MPa). The inclusion of up to 20 volume percent of dicyclohexylamine in the aniline feed, or 1.5–3% by volume of $NH_3$ is recommended. However, no significant improvement is shown in the examples by adding $NH_3$, and the process is said to be inoperative at temperatures below 200° C.

In an article by H. Greenfield (J. Org. Chem. 29, 3082 (1964), a batch hydrogenation of aniline using a ruthenium catalyst is reported. The inclusion of $NH_3$ is said to inhibit the ruthenium catalyst, and the reaction at 145° C. is shown to be impractically slow, and to produce significant quantities of undesirable dicyclohexylamine.

SUMMARY OF THE INVENTION

It has now surprisingly been found that aniline can be efficiently hydrogenated over a ruthenium catalyst to produce cyclohexylamine with a minimum amount of byproduct dicyclohexylamine or cyclohexane by operating at a temperature of from 160° to 180° C. and by including from about 1 to about 8 parts by weight of ammonia per 100 parts aniline by weight in the charge. Moderate hydrogen pressures of from about 2 MPa to 5 MPa can be employed, and the reaction proceeds smoothly to completion in one half hour to four hours, with no rapid rise in temperature or localized heating. The ruthenium catalyst does not appear to be poisoned by the ammonia, and can be recycled a number of times.

DETAILED DESCRIPTION

The ruthenium catalyst is effective in amounts of as little as 0.02 part or less by weight of ruthenium metal based on 100 parts of aniline by weight. While the preferred ruthenium catalyst used in the present invention is ruthenium metal in a finely divided form supported on activated aluminum pellets as described heretofore, it is also possible to disperse the ruthenium on carbon, kieselguhr, or other inert carrier in granular, pelleted, ball, or other fabricated shapes. the ruthenium can be in the elementary form as in the preferred embodiment, as ruthenium oxide or dioxide, or as a salt of ruthenium with ruthenium in either the anion or the cation thereof, in accordance with the teaching of the prior art use of noble metal catalysts. For best results, a supported ruthenium catalyst is used, and 5% ruthenium metal on a carbon support gave good yields and could be efficiently recycled. From 1 to 2% of the supported catalyst by weight, based on the aniline is preferred. Smaller amounts of catalyst give slower reaction times, while larger amounts become prohibitively expensive. The carbon-supported catalyst can be water-wet to suppress dusting.

Ammonia is used in the amount of from 1 to 8, preferably 1.5 to 5, parts by weight per 100 parts of aniline by weight. The ammonia is preferably anhydrous rather than aqueous, as the presence of significant amounts of water in the process of the invention tends to produce cyclohexanol. If, for example, 5 parts of aqueous ammonia were used, assuming 28% $NH_3$ content, 17.9 parts of water would be introduced per 100 parts aniline charged, and this is found to be an unacceptable water level. Ammonia levels below 1 part are less effective in retarding formation of dicyclohexylamine, while an excess of ammonia, above 8 parts, tends to reduce the rate of the reaction below an acceptable economic level.

The temperature of the process of the invention should be controlled between 160° and 180° C. Lower temperatures result in unacceptably slow reaction rates, while temperatures above 180° C. produce not only high levels of dicyclohexylamine but also significant amounts of cyclohexane.

Recommended pressures for the process of the invention are from about 2 to about 5 MPa. Higher pressures, up to 30 MPa or higher, are not necessarily harmful to the process, but require more expensive equipment. Pressures lower than 2 MPa can be used, but may result in reduced reaction rates, especially since a portion of the applied pressure is due to the presence of ammonia in the system.

Under the recommended conditions, reaction times for the process of the invention can range from about one half hour up to about three or four hours. The catalyst can be recycled a number of times before its efficiency drops below acceptable levels. Typically, the catalyst retains its efficiency for at least four batches.

A more complete understanding of the process of the invention can be obtained by reference to the following examples, in which all parts are by weight unless otherwise indicated.

EXAMPLE I

Into a one-liter stainless steel autoclave (Parr, series 4500) equipped with agitator, thermowell, pressure gauge, cooling coils, rupture disc, stainless steel filter element (15μ) and appropriate inlets and vents are charged 200 grams (2.15 moles) aniline and varying amounts of 5% ruthenium on carbon catalyst (Englehard or Johnson Matthey).

The system is purged with nitrogen twice by pressuring to 0.7 MPa (100 psi) and then venting to atmospheric pressure. Varying amounts of anhydrous ammonia are introduced from a lecture bottle, and the contents of the autoclave are heated to 120°–125° C.

Hydrogen pressure is then placed on the system to a total pressure of about 3.5 MPa. An exothermic reaction takes place which is controlled by the application of water on the coils. The hydrogen reacted is replaced by periodic re-pressurization with hydrogen to 3.5 MPa.

After 30 minutes a small sample of filtered reaction mass is taken for G.L.C. analysis, and the amount of aniline remaining is determined. The autoclave is sampled in the same manner every 30 minutes until all the aniline has been reduced. The reaction proceeds smoothly at a relatively constant rate, with no heat buildup.

When the reaction is completed, the contents of the autoclave are cooled to 40°-50° C. and discharged through the filter. A small heel of reaction mixture is left in the autoclave.

For recycle of the catalyst, fresh aniline (again, 200 grams) is drawn into the autoclave, the autoclave is purged with nitrogen as before, ammonia and hydrogen are added as before, and the reaction is repeated.

After several completed batches, the accumulated reaction masses (filtered) are distilled, using a five plate Oldershaw column and a 1/1 reflux ratio to a head temperature of 134°-135° C. A main fraction is collected at 135°-137° C., up to a still pot temperature of 170° C.

Various runs are set forth in Table I, following, using different conditions and amounts of ingredients.

As shown in Table I, runs 1 and 8 contained no ammonia, and were thus outside the scope of the invention. Both 1 and 8 produced high levels of dicyclohexylamine. Runs 6 and 7 were performed at 145° C. and were also outside the scope of the invention, more than one third of the aniline having been unreacted after 4 and 3 hours, respectively, despite the unusually high level of catalyst used. Similarly, run 10, performed at 220° C. was outside the scope of the invention. A high level of dicyclohexylamine was produced in run 10, as well as an appreciable amount of cyclohexane, more than any of the other trials.

The catalyst can be recycled, and in Table I runs 2-5 were successive recycles of the catalyst used in run 1. Similarly, run 7 was a recycle of the catalyst used in run 6, and runs 9-11 were recycles of the catalyst used in run 8. As shown by the poorer results in run 5 (12.4% unreacted aniline, despite a 5 hour reaction time) after four recycles the catalyst began to lose its effectiveness.

Runs 8-11 were made using a water-wet catalyst. This form is preferred for safety and ease of handling, since the dry form is somewhat dusty. The presence of small (2 grams) amount of water does not appear to affect the reaction adversely.

EXAMPLE II

The procedure of Example I is repeated, with the autoclave pressure maintained at 3.45 MPa, and the temperature controlled at 160° C. The first trial is a control identified as run 12 and run with no ammonia present, hence, it is outside the scope of the invention. The catalyst is then recycled twice, in runs 13 and 14 in which 3% ammonia, based on the aniline, is charged. The reaction mass from run 12 is first removed through the filter, leaving a 68.5 gram heel. After the completion of run 13, the reaction mass is taken off as before, leaving a 66.7 gram heel, onto which aniline is charged for run 14.

The progress of the reactions and the results are summarized in Table II following. The initial analysis in each of runs 13 and 14 enabled calculation of the amount of heel left from the previous run. Calculations also showed that run 13 produced 96.3% cyclohexylamine and 1.3% dicyclohexylamine, and that run 14 produced 95.1% cyclohexylamine and 3.9% dicyclohexylamine.

TABLE I

| | Charge | | | | | Reaction Product, by weight % | | | |
|---|---|---|---|---|---|---|---|---|---|
| Run | Aniline, Grams | Catalyst, Grams | NH$_3$, Grams | Temp., °C. | Time, Min. | Cyclohexyl-amine | Cyclo-hexane | Aniline | Dicyclo-hexylamine |
| 1 | 200 | 2.5 | — | 170 | 60 | 89.2 | 1.0 | 0.8 | 9.5 |
| 2 | 200 | 2.5 | 9 | 170 | 150 | 85.1 | 1.5 | 0.1 | 3.3 |
| 3 | 200 | 2.5 | 10 | 170 | 180 | 86.9 | 1.6 | — | 1.6 |
| 4 | 200 | 2.5 | 10 | 170 | 165 | 95.6 | 1.7 | 1.4 | 1.4 |
| 5 | 200 | 2.5 | 10 | 175 | 300 | 82.8 | 2.0 | 12.4 | 2.0 |
| 6 | 200 | 8.0 | 5 | 145 | 240 | 64.0 | 0.4 | 35.8 | 1.7 |
| 7 | 200 | 8.0 | 9 | 145 | 180 | 62.2 | 0.4 | 35.0 | 1.4 |
| 8 | 200 | 2.0* | — | 172 | 83 | 90.0 | 1.0 | — | 9.0 |
| 9 | 200 | 2.0* | 3 | 170 | 60 | 90.6 | 0.8 | 1.0 | 6.3 |
| 10 | 200 | 2.0* | 5 | 220 | 30 | 86.9 | 2.6 | — | 9.8 |
| 11 | 200 | 2.0* | 5 | 170 | 43 | 93.3 | 0.9 | — | 4.8 |

*plus 2 grams water

TABLE II

| | Charge | | | | | Reaction Product, by weight % | | | |
|---|---|---|---|---|---|---|---|---|---|
| Run | Aniline, Grams | Catalyst, Grams | NH$_3$, Grams | Temp., °C. | Time, Min. | Cyclohexyl-amine | Cyclo-hexane | Aniline | Dicyclo-hexylamine |
| 12 | 200 | 2.0 | — | 160 | 0 | ANALYSIS NOT RUN | | | |
| | | | | 160 | 120 | 81.4 | 1.0 | — | 17.5 |
| 13 | 200 | 2.0* | 9.0 | 160 | 0 | 21.1 | — | 74.5 | 4.2 |
| | | | | 160 | 60 | 67.4 | 0.9 | 21.5 | 4.8 |
| | | | | 160 | 101 | 92.3 | 1.5 | 0.6 | 5.4 |
| 14 | 200 | 2.0* | 9.0 | 160 | 0 | 23.4 | 0.2 | 75.0 | 1.2 |
| | | | | 160 | 60 | 76.8 | 0.8 | 18.9 | 2.8 |
| | | | | 160 | 80 | 94.6 | 1.1 | — | 4.3 |

*catalyst contained in heel from previous run

The reactions were observed to be "zero order" reactions, that is, the time rate of reaction was linear, independent of the concentration of reactants or products. No difficulty was experienced in controlling the temperature of the reactions, and no "hot spots" or temperature surges were noted.

The ability to recycle the catalyst several times with no appreciable loss in its efficiency is seen to be an important economic advantage. As demonstrated in the above examples, three or four recycles of the catalyst were accomplished with no diminution of yield or reaction rate.

Cyclohexylamine produced by the process of the invention is a useful chemical intermediate, and can be further reacted to product artificial sweeteners of the cyclamate variety, among other useful materials.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The process of hydrogenating aniline to produce cyclohexylamine comprising subjecting aniline to hydrogen pressure in contact with a ruthenium catalyst in the presence of from about 1 to about 8 parts by weight of ammonia per 100 parts by weight of aniline at an absolute pressure of from about 2 to 5 MPa and at a temperature of from 160° to 180° C.

2. The process of claim 1, wherein the ruthenium catalyst is present in the amount of at least 0.02 parts by weight per 100 parts of aniline by weight.

3. The process of claim 1, wherein the ruthenium catalyst is supported on carbon.

4. The process of claim 3, wherein the catalyst is water-wet.

5. The process of claim 3, wherein the supported catalyst is present in the amount of from about 1 to 4 parts by weight per 100 parts of aniline by weight.

6. The process of claim 1, wherein the ammonia is present in the amount of from 1.5 to 5 parts by weight per 100 parts of aniline by weight.

7. The process of claim 1, wherein the catalyst is recycled at least once.

8. The process of claim 7, wherein the catalyst is recycled at least four times.

* * * * *